(12) United States Patent
Marlowe et al.

(10) Patent No.: US 8,859,525 B2
(45) Date of Patent: Oct. 14, 2014

(54) PHARMACEUTICAL COMPOSITIONS COMPRISING MUSHROOM-BASED POLYSACCHARIDES AND USES THEREOF

(75) Inventors: Zora T. Marlowe, Rochester, NY (US); Paramita Sarkar, Webster, NY (US); Brian J. Glass, Henrietta, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 233 days.

(21) Appl. No.: 13/468,125

(22) Filed: May 10, 2012

(65) Prior Publication Data

US 2013/0023492 A1  Jan. 24, 2013

Related U.S. Application Data

(60) Provisional application No. 61/509,283, filed on Jul. 19, 2011.

(51) Int. Cl.

| | | |
|---|---|---|
| *A61K 31/715* | (2006.01) | |
| *A61K 31/734* | (2006.01) | |
| *A61K 31/736* | (2006.01) | |
| *A61P 37/08* | (2006.01) | |
| *A61P 31/04* | (2006.01) | |
| *A61P 27/02* | (2006.01) | |
| *A61P 29/00* | (2006.01) | |
| *A61K 9/00* | (2006.01) | |
| *A61K 36/07* | (2006.01) | |
| *A61K 9/08* | (2006.01) | |
| *A61K 31/573* | (2006.01) | |
| *A61K 47/26* | (2006.01) | |

(52) U.S. Cl.
CPC ............. *A61K 31/715* (2013.01); *A61K 31/736* (2013.01); *A61K 31/734* (2013.01); *A61K 31/573* (2013.01); *A61K 9/0048* (2013.01); *A61K 36/07* (2013.01); *A61K 47/26* (2013.01); *A61K 9/08* (2013.01)
USPC ......................................................... 514/54

(58) Field of Classification Search
None
See application file for complete search history.

(56) References Cited

U.S. PATENT DOCUMENTS

| | | |
|---|---|---|
| 2,798,053 A | 7/1957 | Brown |
| 4,136,250 A | 1/1979 | Mueller et al. |
| 4,192,827 A | 3/1980 | Mueller et al. |
| 4,804,539 A | 2/1989 | Guo et al. |
| 4,883,658 A | 11/1989 | Holly |
| 4,914,088 A | 4/1990 | Glonek et al. |
| 5,075,104 A | 12/1991 | Gressel et al. |
| 5,278,151 A | 1/1994 | Korb et al. |
| 5,294,607 A | 3/1994 | Glonek et al. |
| 5,371,108 A | 12/1994 | Korb et al. |
| 5,578,586 A | 11/1996 | Glonek et al. |
| 6,447,792 B2 * | 9/2002 | Roulier et al. ................. 424/401 |
| 6,984,628 B2 * | 1/2006 | Bakhit et al. .................. 514/20.8 |
| 8,435,541 B2 * | 5/2013 | Ceccoli et al. ........... 424/195.15 |
| 2006/0222608 A1 | 10/2006 | Yang et al. |

FOREIGN PATENT DOCUMENTS

| | | |
|---|---|---|
| WO | 0132830 A2 | 5/2001 |
| WO | 2011018800 A2 | 2/2011 |

OTHER PUBLICATIONS

PubMed abstract of Kiho, T. et al "Polysaccharides in fungi XXXIII Hypoglycemic activity . . . " Yakagaku Zasshi (1994) vol. 114, No. 5, 308-315.*
Kim, Y. et al "The anti-melanogenic effect of pycnogenol . . . " Food Chem. Toxicol. (2008) vol. 46, pp. 2466-2471.*
Torsdottir, I. et al "A small dose of soluble alginate-fiber . . . " J. Nutr. (1991) vol. 121, pp. 795-799.*
Debaets et al., "Extracellular Tremella polysaccharides: structure, properties and applications," Biotech Letters, 2001, (vol. 23), (p. 1361-1366).
Goodman & Gilman's, "The Pharmacological Basis of Therapeutics," 2006, 11 ed., McGraw-Hill (New York NY).
Martindale, "The Complete Drug Reference," 2005, 34 ed., Pharmaceutical Press (London), (p. 1411-1416).
Remington, "Coarse Dispersions," Chapter 22, 2006, (p. 319-337).

* cited by examiner

*Primary Examiner* — Leigh Maier
(74) *Attorney, Agent, or Firm* — Toan P. Vo

(57) ABSTRACT

A composition for providing relief to a discomfort of an eye comprises a pharmaceutically acceptable carrier and a polysaccharide extracted from a plant source. In certain embodiments, such a polysaccharide can be extracted from mushrooms, such as from the *Tremella fuciformis* species. The composition is administered to an affected eye to provide such relief or discomfort.

22 Claims, 7 Drawing Sheets

PHARMACEUTICAL COMPOSITIONS COMPRISING MUSHROOM-BASED POLYSACCHARIDES AND USES THEREOF

CROSS REFERENCE

This application claims the benefit of U.S. Provisional Patent Application No. 61/509,283 filed Jul. 19, 2011, which is incorporated by reference herein.

BACKGROUND OF THE INVENTION

The present invention relates to pharmaceutical compositions comprising polysaccharides extracted from a plant source and their uses. In particular, the present invention relates to ophthalmic pharmaceutical compositions comprising a polysaccharide extracted from a plant source and their uses to provide relief to eye conditions such as eye discomfort or irritation. More particularly, the present invention relates to ophthalmic pharmaceutical compositions comprising a polysaccharide extracted from mushrooms and their use to provide relief to a dry eye condition.

Many environmental factors can negatively affect the health of the eye. For example, allergens, irritants (such as chemicals), viruses, and bacteria can result in redness, irritation, or inflammation of the conjunctiva. Diseases from other parts of the body also can affect the eye. Dry eye (also known as keratoconjunctivitis sicca ("KCS")), a disorder manifested as insufficient tear film for lubrication of the ocular surface, can be the result of environmental factors or diseases. Dry eye affects millions of people each year. There has been increasing evidence that inflammation may be an important factor in the pathogenesis of KCS. For example, inflammation of the lacrimal and meibomian glands can curb tear production. In addition, elevated levels of pro-inflammatory mediators, including IL-1, have been detected in the conjunctival tissues of patients afflicted with systemic autoimmune diseases, such as Sjögren's syndrome. Sjögren's syndrome is a chronic disorder in which white blood cells attack the moisture-producing glands, such as lacrimal and salivary glands. Dry eye may afflict individuals with differing severity. In mild cases, a patient may experience burning, a feeling of dryness, and other symptoms of ocular discomfort. In severe cases, vision may be substantially impaired. Although dry eye may have a variety of unrelated pathogenic causes, they all share as a common effect the breakdown of the ocular tear film, with dehydration of and subsequent damage to the exposed outer ocular surfaces.

These pathological conditions produce significant discomfort in the eye, such as itching or burning sensation, which can benefit from relief by palliative agents. Many such agents have been provided with varying success. The relief that they provide are often short-lived. In addition, prior-art compositions do not effectively provide many benefits of the natural tear. Therefore, there is a continued need to provide improved ophthalmic compositions for the relief of ocular discomfort. It is also very desirable to provide such compositions for an extended relief of ocular discomfort such as the dry eye condition.

SUMMARY OF THE INVENTION

In general, the present invention provides pharmaceutical compositions comprising a polysaccharide extracted from a plant source.

In one aspect, the present invention provides pharmaceutical compositions comprising a polysaccharide extracted from mushrooms.

In another aspect, the present invention provides pharmaceutical compositions comprising a polysaccharide extracted from mushrooms for relieving discomfort in an eye.

In still another aspect, such discomfort results from an ocular condition, such as allergy, infection, inflammation, or dry eye syndrome.

In yet another aspect, the present invention provides ophthalmic pharmaceutical compositions comprising a polysaccharide extracted from mushroom for relieving the dry eye syndrome.

In still another aspect, the present invention provides ophthalmic pharmaceutical compositions for relieving ocular discomfort resulting from a treatment of another condition of the eye, such as an eye surgery (e.g., glaucoma surgery, cataract surgery, or surgery to treat a back-of-the-eye condition).

In still another aspect, an ophthalmic pharmaceutical composition of the present invention comprises a material that allows the composition to remain on an ocular surface for an extended period of time.

In a further aspect, the present invention provides an ophthalmic composition for relieving discomfort resulting from an ocular condition, such as allergy, infection, inflammation, dry eye syndrome, or combinations thereof: wherein the composition comprises a polysaccharide extracted from a plant source.

In still another aspect, the present invention provides an ophthalmic composition for relieving discomfort resulting from an ocular condition, such as allergy, infection, inflammation, dry eye syndrome, or combinations thereof; wherein the composition comprises a polysaccharide comprises or is glucuronoxylomannan or variant thereof extracted from mushrooms. A variant of glucuronoxylomannan means a polysaccharide comprising additional monosaccharide units other than the mannose backbone chain and glucuronic acid and xylose units in its side chains.

In yet another aspect, the present invention provides an ophthalmic composition for relieving the dry eye syndrome; wherein the composition comprises a polysaccharide comprises or is glucuronoxylomannan or a variant thereof extracted from mushrooms.

In yet another aspect, the present invention provides an ophthalmic composition for relieving the dry eye syndrome; wherein the composition comprises a polysaccharide comprises or is extracted from the mushroom *Tremella* species.

In still another aspect, the present invention provides an ophthalmic composition for relieving the dry eye syndrome; wherein the composition comprises a polysaccharide comprises or is extracted from the mushroom species *Tremella fuciformis*.

In yet another aspect, any ophthalmic pharmaceutical composition disclosed herein is devoid of preservatives that can produce discomfort in the eye.

In a further aspect, any ophthalmic pharmaceutical composition of the present invention, as disclosed herein, is devoid of preservatives.

In yet another aspect, the present invention provides a method for relieving discomfort of the dry eye syndrome, the method comprising administering into an affected eye a composition that comprises a pharmaceutically (or particularly, ophthalmically) acceptable carrier and a polysaccharide extracted from a plant source.

In yet another aspect, the present invention provides a method for relieving discomfort in an eye such as the dry eye syndrome, the method comprising administering into an affected eye a composition that comprises a material that allows the composition to remain on an ocular surface for an extended period of time; wherein said material comprises a polysaccharide extracted from a plant source (such as glucuronoxylomannan or variant thereof extracted from mushrooms).

Other features and advantages of the present invention will become apparent from the following detailed description and claims.

DETAILED DESCRIPTION

Figure 1:
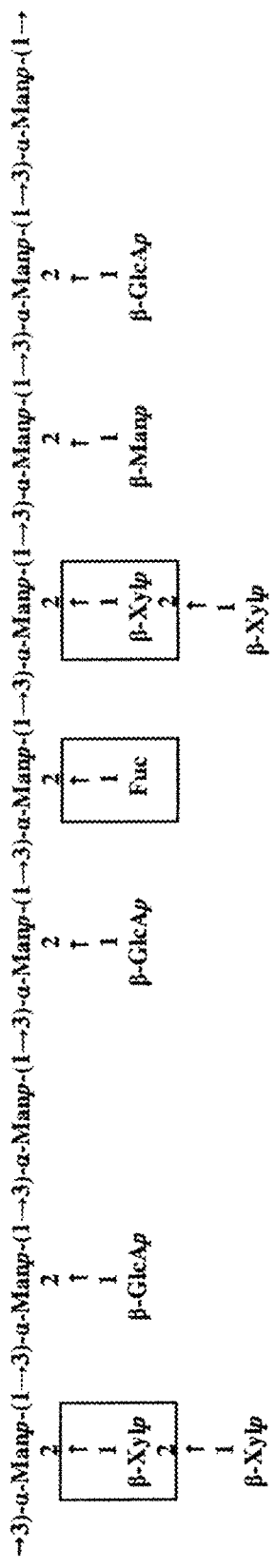
FIG. 1 is a schematic representation of TFP (Baets, 2001) (DeBaets, S. & Vandamme, E. J. (2001). Extracellular *Tremella* Polysaccharides: Structure, Properties and Applications. Biotechnology Letters, 23, 1361-1366.)
Figure 2:
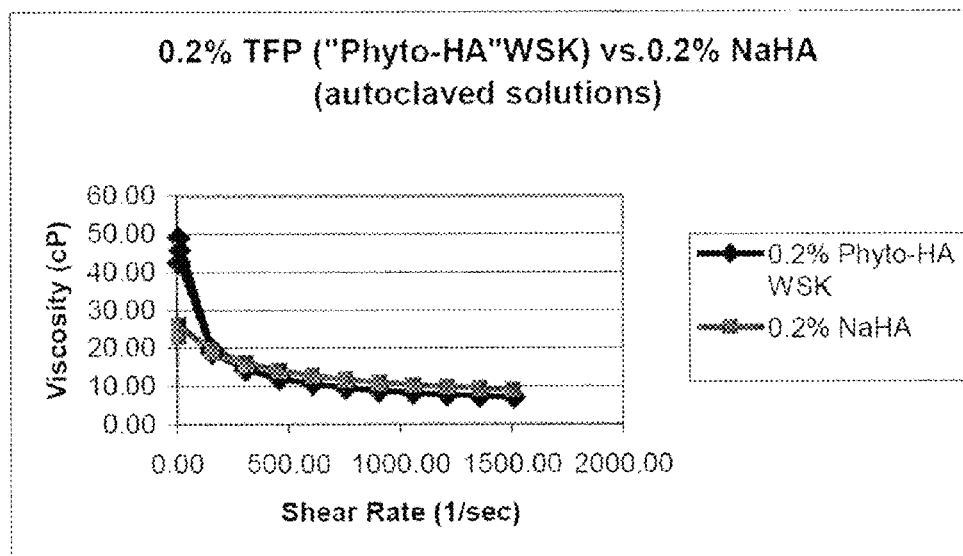
FIG. 2 shows at low shear the increased viscosity and enhanced shear thinning of the TFP vs. the sodium HA with both being considered the same molecular weight.

In general, the present invention provides pharmaceutical compositions comprising a polysaccharide extracted from a plant source.

Such compositions can many uses in treating or ameliorating diverse disorders of the human body, such as those affecting joints, eyes, digestive tracts, skin, wounds, etc.

In one aspect, the present invention provides pharmaceutical compositions comprising a polysaccharide extracted from mushrooms. In one embodiment, the present invention provides pharmaceutical compositions comprising a polysaccharide extracted from mushrooms for treating or ameliorating diverse disorders of the human body, such as those affecting joints, eyes, digestive tracts, skin, wounds, etc.

In another aspect, the present invention provides pharmaceutical compositions comprising a polysaccharide extracted from mushrooms for relieving discomfort in an eye.

In still another aspect, such discomfort results from an ocular condition, such as allergy, infection, inflammation, or dry eye syndrome.

In yet another aspect, the present invention provides ophthalmic pharmaceutical compositions comprising a polysaccharide extracted from mushroom for relieving the dry eye syndrome.

In still another aspect, an ophthalmic pharmaceutical composition of the present invention comprises a material that allows the composition to remain on an ocular surface for an extended period of time.

In still another aspect, an ophthalmic pharmaceutical composition of the present invention can comprise a demulcent.

In a further aspect, the present invention provides an ophthalmic composition for relieving discomfort resulting from an ocular condition, such as allergy, infection, inflammation, dry eye syndrome, or combinations thereof; wherein the composition comprises a polysaccharide extracted from a plant source.

In yet another aspect, the present invention provides an ophthalmic composition for relieving discomfort resulting from an ocular condition, such as allergy, infection, inflammation, dry eye syndrome, or combinations thereof; wherein the composition comprises a polysaccharide comprises or is extracted from the mushroom *Tremella* species.

In yet another aspect, the present invention provides an ophthalmic composition for relieving discomfort resulting from an ocular condition, such as allergy, infection, inflammation, dry eye syndrome, or combinations thereof; wherein the composition comprises a polysaccharide comprises or is extracted from the mushroom species selected from the group consisting of *Tremella fuciformis, Tremella mesenterica, Tremella aurantia*, mixtures thereof, and combinations thereof.

In still another aspect, the present invention provides an ophthalmic composition for relieving discomfort resulting from an ocular condition, such as allergy, infection, inflammation, dry eye syndrome, or combinations thereof; wherein the composition comprises a polysaccharide extracted from mushroom species (such as the *Tremella* species), which polysaccharide comprises a backbone chain of (1→3)α-linked mannose units and side chains comprising β-linked glucuronic acid and/or xylose units; wherein some of the carboxylic acid moieties of the glucuronic acid units may be acetylated. The side chains of these polysaccharides may also contain other saccharide units, such as glucose and fucose.

In still another aspect, the present invention provides an ophthalmic composition for relieving discomfort resulting from an ocular condition, such as allergy, infection, inflammation, dry eye syndrome, or combinations thereof; wherein the composition comprises a polysaccharide comprises or is glucuronoxylomannan extracted from mushrooms.

The mushroom polysaccharides can be grouped as glucuronoxylomannans and have high molecular weight and can be used as rheology modifiers for pharmaceutical, lens care and surgical applications. In addition, the specific polysaccharide tested has surprising wetting ability and imparts hitherto unknown functional properties to novel ophthalmic lipid-based products.

A heterosaccharide derived from *Tremella* mushroom extract (or *Tremella fuciformis* polysaccharide, abbreviated as "TFP"), considered all natural, with molecular weight of ≥1 M Da, shows increased viscosity and improved shear thinning as well as increased stability upon autoclaving over sodium HA (molecular weight 1.2 M Da.) The linear glucuronoxylomannan consists of a mannose (α, 1-3 linkage) backbone with xylose and glucuronic acid along with fucose, glucose and other sugar residues attached to the backbone[1]. The high content of glucuronic acid of the polymer makes it similar to hyaluronic acid[2,3]. The polymer has also been shown to have a high degree of water-binding capacity compared to hyaluronate[3]. A schematic representation of the structure of TFP is shown in FIG. 1. Other mannan polysaccharides from other *Tremella* species may also be suitable for such pharmaceutical and ophthalmic formulations.

Rheological studies with *Tremella* polysaccharides have shown them to exhibit viscoelasticity, shear-thinning characteristics[4]. These properties are not greatly affected by the presence of ions. In addition the viscosity of the polymer is maintained after exposure to high temperatures[4]. These characteristics of the polymer indicate that it would be a versatile excipient for pharmaceutical applications with special use in the area of ophthalmic formulations.

In addition to the above-mentioned qualities, we have also found that *Tremella* polysaccharide, TFP, shows surprisingly good wetting ability on contact lens surface, can be combined with alginate to improve mucin interaction in the presence of ions and plays an enhancing role for the delivery of certain lipids to a synthetic meibum layer in a Langmuir Film Balance experiment.

Autoclave Experiments Data

Solutions of mushroom extract ("Phyto-HA" WSK, Applechem, Inc. (although this extract is called "Phyto-HA" by the manufacturer, it should be noted that it is merely a name, and not necessarily a representation of its chemical nature)) and sodium hyaluronate were prepared as 1% w/w solution in deionized water, along with 3% w/w mannitol. The polymer solutions were diluted (9 parts polymer solution to 1 part of 4% w/w sodium citrate, dihydrate.) For each polymer, two bottles were prepared: one bottle of the 0.9% polymer solution sat at room temperature overnight, while the other was autoclaved (121° C. for 30 minutes).

The viscosities of the 0.9% solutions of sodium hyaluronate (Na HA) and TFP were measured before and after autoclaving. The table below shows the average (x=3) viscosity for the solutions when measured at a shear rate of 7.5 $\sec^{-1}$. A Brookfield RV DVIII viscometer was used for the measurements. The spindle used was a CPE-40, with 0.5 mL sample size, at 25° C.

TABLE 1

Viscosity and GPC data[5] of three polymers autoclaved with or without polypropylene glycol (P425).

| Sample ID | Description | Auto-claved | Mw | Mn | PD | pH* | Viscosity* (mPa · s) | % viscosity remaining after auto-claving |
|---|---|---|---|---|---|---|---|---|
| | Sodium alginate LF-200M raw material | N | 197,000 | 83,000 | 2.38 | N/A | N/A | |
| 3089 ZTM-97-7 | 0.5% Na-Alg +9.5% P425 w borate buffer | N | 228000 | 77000 | 3.02 | 7.75 | 36 | — |
| 3089-ZTM-97-4 | 5% Na-Alg +95% P425→ autoclave → dil w borate buffer (final alg. Conc. 0.5%: 9.5% P425) | Y (before diln) | 132000 | 44,000 | 3.01 | 7.60 | 18 | 50% |
| 3089-ZTM-97-1 | 5% Na-Alg +95% water → autoclave → dil with 9.5% P425 + borate buffer (final Alg conc. 0.5%; 9.5% P425 | Y | 90,000 | 39,000 | 2.34 | 7.72 | 8.18 | 22.7% |
| | Sodium hyaluronate (MW > 1 MDa) raw material | N | 1,654,000 | 1,076,000 | 1.54 | NA | NA | |
| 3089 ZTM-97-8 | 0.5% Na-HA +9.5% P425 w borate buffer | N | 1,827,000 | 1,1174,000 | 1.56 | 7.79 | 620 | — |
| 3089-ZTM-97-5 | 5% Na-HA +95% P425→autoclave → dil w borate buffer (final HA conc. 0.5%; 9.5% P425) | Y (before diln) | 3,232.000 | 2,188,000 | 1.48 | 7.57 | 468 | 75.4% |
| 3089-ZTM-97-2 | 5% Na-HA +95% water→autoclave→ dil w 9.5% P425 + borate buffer(final HA conc. 0.5%; 9.5% P425) | Y | 808,000 | 521,000 | 1.55 | 7.77 | 182 | 29.35% |
| | Tremella polysachharide or TFP ["Phyto-HA"] (MW > 1 MDa) raw material | N | 3,927,000 | 2,864,00 | 1.37 | N/A | N/A | |

TABLE 1-continued

Viscosity and GPC data[5] of three polymers autoclaved with or without polypropylene glycol (P425).

| Sample ID | Description | Auto-claved | Mw | Mn | PD | pH* | Viscosity* (mPa·s) | % viscosity remaining after autoclaving |
|---|---|---|---|---|---|---|---|---|
| 3089-ZTM-97-9 | 0.5% TFP +9.5% P425 w borate buffer | N | 4,015,000 | 3,394,000 | 1.18 | 7.79 | 551 | — |
| 3089-ZTM-97-6 | 5% TFP +95% P425→autoclave→ dil w borate buffer (final TFP conc. 0.5%; 9.5% P425) | Y (before diln) | 3,146,000 | 2,090,000 | 1.51 | 7.61 | 449 | 90.6% |
| 3089-ZTM-97-3 | 5% TFP +95% water→autoclave→ dil w 9.5% P425 in borate buffer (final TFP conc 0.5%; 9.5% P425) | Y (before diln) | 2,783,000 | 1,647,000 | 1.69 | 7.7 | 373 | 67.7% |

*Notebook ref#3089-ZTM-93-99,102-105 The autoclaved solutions were further diluted with deionized water to 0.2% w/w. These solutions were measured on a forward-reverse shear program on the Brookfield viscometer (at 25° C.).

Glucuronoxylomannan from *Tremella fuciformis* has been used in several personal care products, but has not been used in ophthalmic products.

Captive Bubble Analysis: Determination of Wetting Ability of Polymer for a Contact Lens Surface Various polymers were analyzed using the captive bubble technique to compare wettability/sustainable wettability after washout. Attached are the plots. The polymers included arahinogalactan, Na HA (sterile filtered), Na HA (autoclaved), Na alginate, Gellan, and TFP (which was autoclaved.) The polymers were dispersed in water, and tonicity was adjusted with mannitol.

Figure 3:
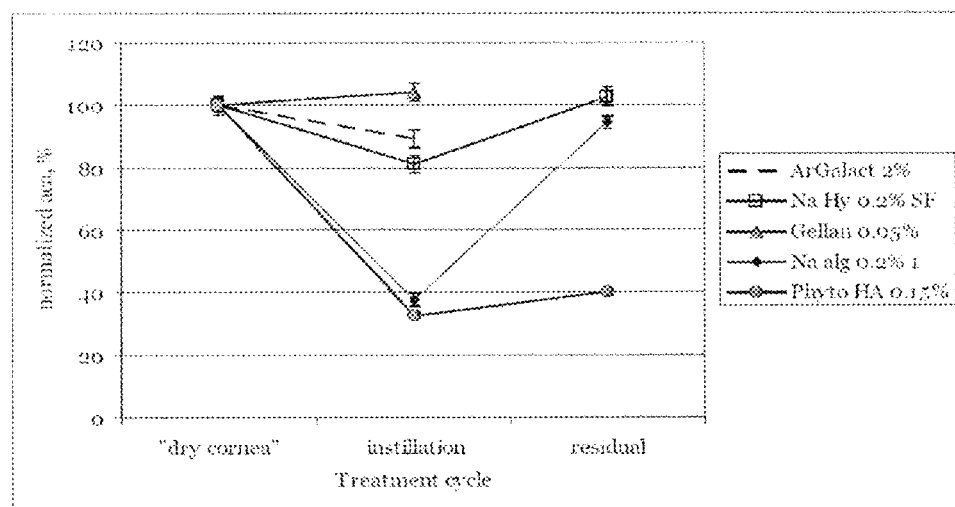
FIG. 3 shows the relative improvement in wettability of a contact lens surface after exposure to various polymer solutions, immediately after instillation and after a wash-out cycle. TFP shows both an immediate improvement and sustained effect after the wash-out.

The captive bubble results indicate that TFP demonstrated a sustainable improvement in wettability after wash-out over the other polymers tested. See FIG. 3.

Modification of Rheological Behavior of Another Polymer

Figure 4:
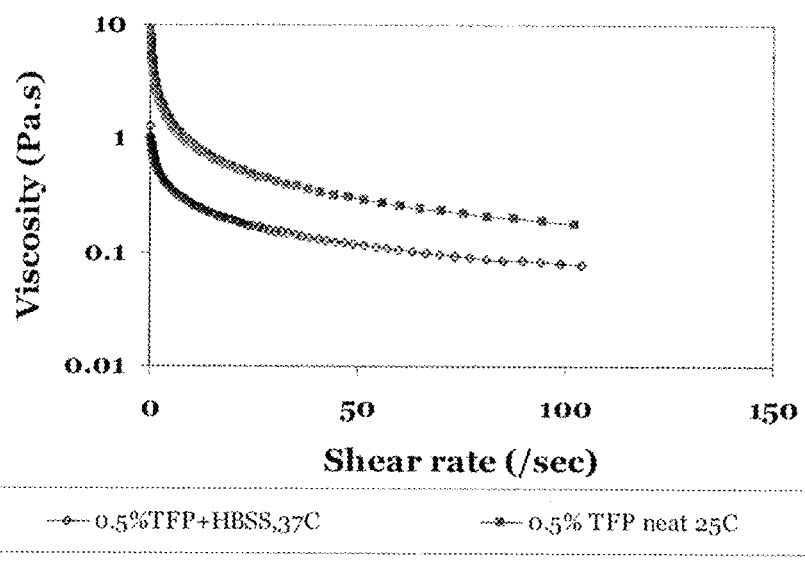
FIG. 4 shows the rheological profile of 0.5% TFP in 3% mannitol, neat or after dilution with HBSS.

In order to see how a combination with an anionic polymer may result in modification of the rheological behavior of that polymer, we investigated the effect of combining TFP with sodium alginate (Na-Alg; LF200M, FMC Inc.). FIG. 4 shows the rheological behavior of 0.5% TFP neat at 25C and after 4:1 dilution with HBSS (hank's balanced salt solution). As we can see, under both conditions, TFP maintains an appreciable viscosity (≥1000 mPa·s) and is shear-thinning.

Figure 5:
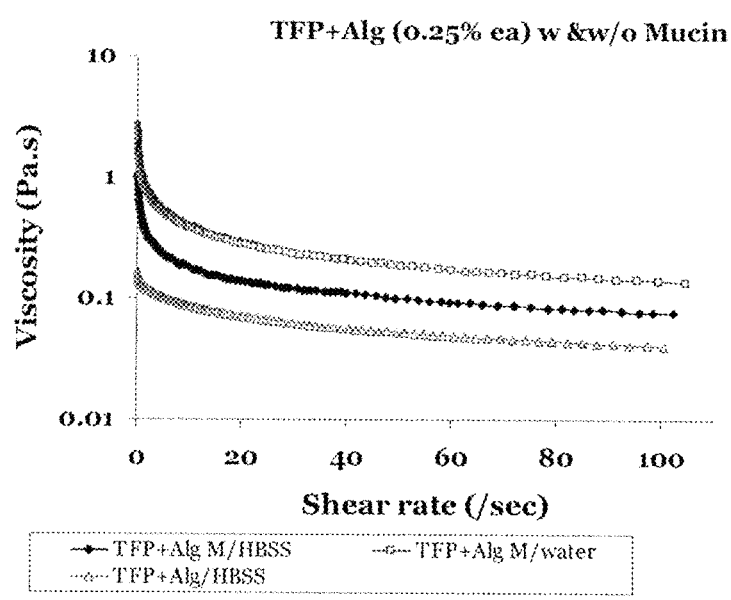
FIG. 5 shows the rheological behavior of TFP+Na-Alginate in the presence of a simulated tear fluid, HBSS, and with mucin prepared in HBSS or in water.
Figure 6:
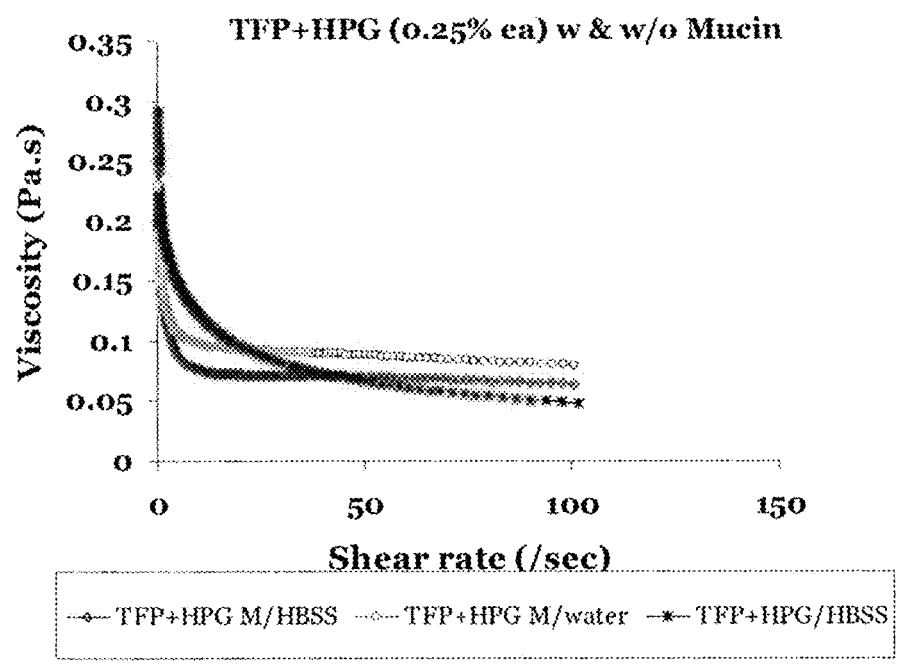
FIG. 6 shows the rheological behavior of TFP+hydroxypropyl guar (HPG) in the presence of a simulated tear fluid, HBSS, and with mucin prepared in HBSS or in water.

Sodium alginate (Na-Alg) is known to be very susceptible to losing viscosity very quickly in the presence of high concentration of ions. Na-Alg is also known to have a high interaction with mucin but, the degree of interaction can vary greatly depending on the mucin quality. It is known that a formulation which is shear-thinning and can have a high mucin interaction can be beneficial for topical ophthalmic delivery, especially dry eye therapy. We therefore studied the effect of ions on TFP and TFP-alginate combinations in the presence of mucin. Mucin stock solutions were prepared in water or HBSS. The polymer solutions were diluted 4:1 with mucin in water or mucin in HBSS. The combination of TFP and alginate led to a polymer mixture that retains appreciable viscosity at rest under all conditions, shows mucoadhesion and is very shear-thinning (FIG. 5). Such properties make the TFP+Alginate mixtures ideal for ophthalmic applications including dry eye therapy. Similar properties were also obtained with TFP+HPGuar (FIG. 6), although the interaction with mucin was not as high as with TFP+Alg mixtures.

Figure 7:
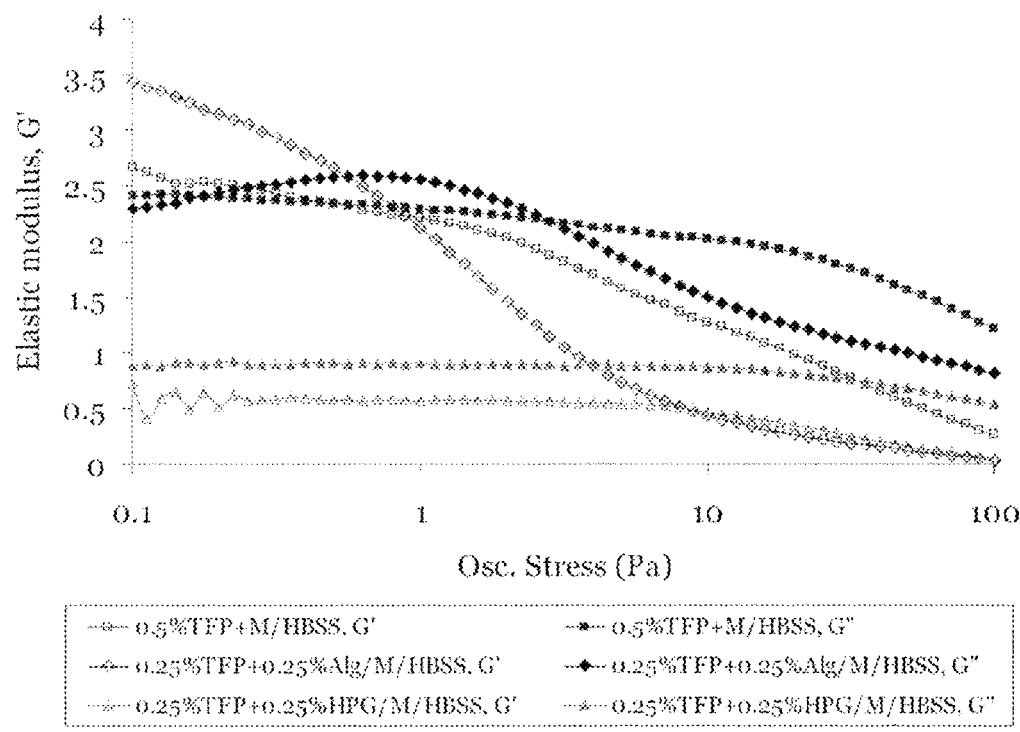
FIG. 7. Amplitude sweep studies on TFP+mucin, TFP+Alg with mucin and TFP+HPG with mucin. TFP+Alg shows the strongest interaction with mucin especially at low oscillatory stresses. TFP+HPG showed very weak viscoelastic properties when combined with mucin.

A comparison of the viscoelastic properties of TFP alone with mucin in HBSS, TFP+Alginate with mucin in HBSS and TFP+HPG with mucin in HBSS is shown in FIG. 7. An amplitude sweep was performed on the mixtures using a parallel plate attachment on a TA AR2000 instrument. Oscillatory stress from 0.1 to 100 Pa was applied at an angular frequency of 10 rad/s. Measurements were done at 37° C. As can be seen from the amplitude sweep, the elastic and viscous moduli for TFP+Alg mixtures were the highest, compared to TFP alone or TFP+HPG when combined with mucin in HBSS.

In another aspect, any composition of the present invention, as disclosed herein, can include a demulcent that provides an extended residence time on an ocular surface after the composition has been administered to said ocular surface. As used herein, the phrase "an extended residence time" or "an extended period of time" means a period of time of at least 30 minutes; preferably, at least 1 hour. A demulcent can be a material that is water soluble, sparingly soluble, or substantially soluble in water. A demulcent that is sparingly soluble or substantially insoluble in water and still absorb water. In one embodiment, such a material is selected from the group consisting of lightly cross-linked, carboxyl-containing polymers that are substantially insoluble or only sparingly soluble in water. In another embodiment, the material is selected from the group consisting of cellulose derivatives (such as sodium carboxymethyl cellulose, hydroxyethyl cellulose, hydroxypropylmethyl cellulose, or methyl cellulose), dextran 70, gelatin, polyethylene glycol, propylene glycol, polyvinyl alcohol, polyvinylpyrrolidone, polyacrylic acid, polymethacrylic acid, combinations thereof, and mixtures thereof. A preferred material comprises a Carbopol polymer, such as Carbopol 980 or Carbopol 976. Other suitable materials include, but are not limited to, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like and can be used in addition to, or instead of, acrylic acid.

Such polymers may be crosslinked by a polyfunctional crosslinking agent, preferably a difunctional crosslinking agent. The amount of crosslinking should be sufficient to form polymers that are substantially insoluble or sparingly soluble in water. Typically the polymers are only lightly crosslinked. Preferably, the crosslinking agent is used in an amount of from about 0.01% to about 5%, preferably from about 0.1% to about 2%, and more preferably from about 0.2% to about 1%, based on the total weight of monomers present. Included among such crosslinking agents are non-polyalkenyl polyether difunctional crosslinking monomers such as divinyl glycol; 2,3-dihydroxyhexa-1,5-diene; 2,5-dimethyl-1,5-hexadiene; divinylbenzene; N,N-diallylacrylamide; N,N-diallymethacrylamide and the like. Also included are polyalkenyl polyether crosslinking agents containing two or more alkenyl ether groupings per molecule, preferably alkenyl ether groupings containing terminal $H_2C=C<$ groups, prepared by etherifying a polyhydric alcohol containing at least four carbon atoms and at least three hydroxyl groups with an alkenyl halide such as allyl bromide or the like; e.g., polyallyl sucrose, polyallyl pentaerythritol, or the like; see, e.g., Brown U.S. Pat. No. 2,798,053, the entire contents of which are incorporated herein by reference. Diolefinic non-hydrophilic macromeric crosslinking agents having molecular weights of from about 400 to about 8,000, such as insoluble di- and polyacrylates and methacrylates of diols and polyols, diisocyanate-hydroxyalkyl acrylate or methacrylate reaction products of isocyanate terminated prepolymers derived from polyester diols, polyether diols or polysiloxane diols with hydroxyalkylmethacrylates, and the like, can also be used as the crosslinking agents; see, e.g., Mueller et al. U.S. Pat. Nos. 4,192,827 and 4,136,250, the entire contents of each patent being incorporated herein by reference.

Such a polymer is present in a composition of the instant invention in an amount from about 0.01 to about 5% (by weight). Alternatively, such a polymer is present in an amount from about 0.01 to about 2%, or from about 0.01 to about 1%, or from about 0.01 to about 0.5%, or from about 0.01 to about 0.2%, or from about 0.01 to about 0.1% (by weight).

In one embodiment, a composition of the present invention is in a form of a suspension or dispersion. In another embodiment, the suspension or dispersion is based on an aqueous solution. For example, a composition of the present invention can comprise sterile saline solution. In still another embodiment, the suspension or dispersion is an oil-based formulation. For example, the formulation can include an oil selected from the group consisting of vegetable oil, peanut oil, olive oil, coconut oil, sesame oil, cottonseed oil, corn oil, sunflower oil, fish-liver oil, arachis oil, liquid paraffin, and mixtures thereof. In still another aspect, a composition of the present invention is an emulsion (oil-in-water (water being the continuous phase) or water-in-oil emulsion (oil being the continuous phase)).

In another aspect, a composition of the present invention can further comprise a non-ionic surfactant, such as polysorbates (such as polysorbate 80 (polyoxyethylene sorbitan monooleate), polysorbate 60 (polyoxyethylene sorbitan monostearate), polysorbate 20 (polyoxyethylene sorbitan monolaurate), commonly known by their trade names of Tween® 80, Tween® 60, Tween® 20), poloxamers (synthetic block polymers of ethylene oxide and propylene oxide, such as those commonly known by their trade names of Pluronic®; e.g., Pluronic® F127 or Pluronic® F108)), or poloxamines (synthetic block polymers of ethylene oxide and propylene oxide attached to ethylene diamine, such as those commonly known by their trade names of Tetronic®; e.g., Tetronic® 1508 or Tetronic® 908, etc., other nonionic surfactants such as Brij®, Myrj®, and long chain fatty alcohols (i.e., oleyl alcohol, stearyl alcohol, myristyl alcohol, docosohexaenoyl alcohol, etc.) with carbon chains having about 12 or more carbon atoms (e.g., such as from about 12 to about 24 carbon atoms). Such compounds are delineated in Martindale, $34^{th}$ ed., pp 1411-1416 (Martindale, "The Complete Drug Reference," S. C. Sweetman (Ed.), Pharmaceutical Press, London, 2005) and in Remington, "The Science and Practice of Pharmacy," $21^{st}$ Ed., p. 291 and the contents of chapter 22, Lippincott Williams & Wilkins, New York, 2006); the contents of these sections are incorporated herein by reference. The concentration of a non-ionic surfactant, when present, in a composition of the present invention can be in the range from about 0.001 to about 5 weight percent (or alternatively, from about 0.01 to about 4, or from about 0.01 to about 2, or from about 0.01 to about 1 weight percent).

In addition, a composition of the present invention can include additives such as buffers, diluents, carriers, adjuvants, or excipients. Any pharmacologically acceptable buffer suitable for application to the eye may be used. Other agents may be employed in the composition for a variety of purposes. For example, buffering agents, surfactants, co-solvents, humectants, emollients, stabilizers, chelating agents, or antioxidants may be employed. Suitable water-soluble buffering agents that may be employed are sodium carbonate, sodium borate, sodium phosphate, sodium acetate, sodium bicarbonate, etc., as approved by the United States Food and Drug Administration ("US FDA") for the desired route of administration. These agents may be present in amounts sufficient to maintain a pH of the system of between about 2 and about 11. As such the buffering agent may be as much as about 5% on a weight to weight basis of the total composition. Electrolytes such as, but not limited to, sodium chloride and potassium chloride may also be included in the formulation.

In one aspect, the pH of the composition is in the range from about 4.5 to about 11. Alternatively, the pH of the composition is in the range from about 6 to about 9, or from about 6.5 to about 8, or from about 6.5 to about 7.5. In another aspect, the composition comprises a buffer having a pH in one of said pH ranges.

In another aspect, the composition has a pH of about 7. Alternatively, the composition has a pH in a range from about 7 to about 7.5.

In still another aspect, the composition has a pH of about 7.4.

In a further aspect, a composition of the present invention formulated for the treatment of dry eye-type diseases, syndromes, or disorders may also comprise carriers designed to provide immediate, short-term relief of dry eye-type conditions. Such carriers can be formulated as a phospholipid carrier or an artificial tears carrier, or mixtures of both. A phospholipid carrier comprises one or more phospholipids that lubricate, wet, approximate the consistency of endogenous tears, aid in natural tear build-up, or otherwise provide temporary relief of dry eye symptoms and conditions upon ocular administration. Non-limiting examples of phospholipid carrier formulations include those disclosed in U.S. Pat. Nos. 4,804,539; 4,883,658; 4,914,088; 5,075,104; 5,278,151; 5,294,607; 5,371,108; 5,578,586; the foregoing patents are incorporated herein by reference to the extent they disclose phospholipid compositions useful as phospholipid carriers of the present invention.

In yet another aspect, a composition also can comprise a viscosity-modifying compound designed to lubricate, wet, approximate the consistency of endogenous tears, aid in natural tear build-up, or otherwise provide temporary relief of dry eye symptoms and conditions upon ocular administration the eye. Such compounds may enhance the viscosity of the composition, and include, but are not limited to: monomeric polyols, such as, glycerol, propylene glycol, ethylene glycol; polymeric polyols, such as, polyethylene glycol; various polymers of the cellulose family, such as hydroxypropylmethyl cellulose ("HPMC"), carboxymethyl cellulose ("CMC") sodium, hydroxypropyl cellulose ("HPC"); polysaccharides other than glucuronoxylomannan and its salts, such as alginate, chondroitin sulfate and its salts, dextrans, such as, dextran 70; water soluble proteins, such as gelatin; vinyl polymers, such as, polyvinyl alcohol, polyvinylpyrrolidone, povidone; carbomers, such as carbomer 934P, carbomer 941, carbomer 940, or carbomer 974P; and acrylic acid polymers. In general, a desired viscosity can be in the range from about 1 to about 2000 centipoises ("cps" or mPa·s), or from about 1 to about 1000 cps, or from about 1 to about 500 cps, or from about 1 to about 200 cps, or from about 1 to about 100 cps. In one embodiment, a viscosity-modifying compound is water soluble. The foregoing viscosity values are measured by a Brookfield Engineering viscometer with a CP-40 or CP-52 spindle, 0.5 mL sample size, at a shear rate of 5-15 sec$^{-1}$ at 25° C.

In still another aspect, a method for preparing a composition of the present invention comprises combining a polysaccharide extracted from a plant source and a pharmaceutically (more particularly, ophthalmically) acceptable carrier. In one embodiment, such a carrier can be sterile water, a sterile saline solution, or a physiologically acceptable buffer.

In yet another aspect, a method for preparing a composition of the present invention comprises combining a glucuronoxylomannan or variant thereof extracted from mushroom and a pharmaceutically (more particularly, ophthalmically) acceptable carrier selected from the group consisting of sterile water, a sterile saline solution, and physiologically acceptable buffers.

In still a further aspect, a method for preparing a composition of the present invention comprises combining: (a) a glucuronoxylomannan or variant thereof extracted from mushroom; (b) a pharmaceutically (more particularly, ophthalmically) acceptable carrier selected from the group consisting of sterile water, a sterile saline solution, and physiologically acceptable buffers; and (c) optionally any pharmaceutically (more particularly, ophthalmically) acceptable ingredients that can provide at least one physiological benefit to the patient, such as a vitamin, an anti-oxidant, an analgesic, or a medicament that is used to treat an ophthalmic disorder other than dry eye.

Physiologically acceptable buffers include, but are not limited to, a phosphate buffer or a Tris-HCl buffer (comprising tris(hydroxymethyl)aminomethane and HCl). For example, a Tris-HCl buffer having pH of 7.4 comprises 3 g/l of tris(hydroxymethyl)aminomethane and 0.76 g/l of HCl. In yet another aspect, the buffer 10× phosphate buffer saline ("PBS") or 5×PBS solution.

Other buffers also may be found suitable or desirable in some circumstances, such as buffers based on HEPES (N-{2-hydroxyethyl}peperazine-N'-{2-ethanesulfonic acid}) having pK$_a$ of 7.5 at 25° C. and pH in the range of about 6.8-8.2; BES (N,N-bis{2-hydroxyethyl}2-aminoethanesulfonic acid) having pK$_a$ of 7.1 at 25° C. and pH in the range of about 6.4-7.8; MOPS (3-{N-morpholino}propanesulfonic acid) having pK$_a$ of 7.2 at 25° C. and pH in the range of about 6.5-7.9; TES (N-tris{hydroxymethyl}-methyl-2-aminoethanesulfonic acid) having pK$_a$ of 7.4 at 25° C. and pH in the range of about 6.8-8.2; MOBS (4-{N-morpholino}butanesulfonic acid) having pK$_a$ of 7.6 at 25° C. and pH in the range of about 6.9-8.3; DIPSO (3-(N,N-bis{2-hydroxyethyl}amino)-2-hydroxypropane)) having pK$_a$ of 7.52 at 25° C. and pH in the range of about 7-8.2; TAPSO (2-hydroxy-3{tris(hydroxymethyl)methylamino}-1-propanesulfonic acid)) having pK$_a$ of 7.61 at 25° C. and pH in the range of about 7-8.2; TAPS ({(2-hydroxy-1,1-bis(hydroxymethyl)ethyl)amino}-1-propanesulfonic acid)) having pK$_a$ of 8.4 at 25° C. and pH in the range of about 7.7-9.1; TABS (N-tris(hydroxymethyl)methyl-4-aminobutanesulfonic acid) having pK$_a$ of 8.9 at 25° C. and pH in the range of about 8.2-9.6; AMPSO (N-(1,1-dimethyl-2-hydroxyethyl)-3-amino-2-hydroxypropanesulfonic acid)) having pK$_a$ of 9.0 at 25° C. and pH in the range of about 8.3-9.7; CHES (2-cyclohexylamino)ethanesulfonic acid) having pK$_a$ of 9.5 at 25° C. and pH in the range of about 8.6-10.0; CAPSO (3-(cyclohexylamino)-2-hydroxy-1-propanesulfonic acid) having pK$_a$ of 9.6 at 25° C. and pH in the range of about 8.9-10.3; or CAPS (3-(cyclohexylamino)-1-propane sulfonic acid) having pK$_a$ of 10.4 at 25° C. and pH in the range of about 9.7-11.1.

A chelating agent may be included in a composition of the present invention. Non-limiting examples of chelating agents that have been used in pharmaceutical formulations include sodium EDTA and hydroxyl alkyl phosphonates (known under the trade name of Dequest®).

In certain embodiments, a composition of the present invention is formulated in a buffer having a slight acidic pH, such as from about 6 to about 6.8. In such embodiments, the buffer capacity of the composition desirably allows the composition to come rapidly to a physiological pH after being administered to into the patient. Alternatively, a composition of the present invention has a pH from about 6.5 to about 7.5.

In still another aspect, a method for providing relief or amelioration to a disorder of a portion of a human body comprises administering a composition comprising a polysaccharide extracted from a plant source (such as from the *Tremella* mushroom species) to said portion of said body that is affected by said disorder at a desired frequency sufficient to provide relief or amelioration to said disorder, such as once every 0.5, 1, 2, 3, 4, 5, 6, 7, 8, 12, or 24 hours. Such frequency is selected to be suitable to the individual patient and its selection is within the ordinary skill of a medical practitioner.

In still another aspect, a method for providing relief to a discomfort of the eye comprises administering a composition comprising a polysaccharide extracted from a plant source (such as from the *Tremella* mushroom species) to said eye at a desired frequency sufficient to provide relief to said discomfort of said eye, such as once every 0.5, 1, 2, 3, 4, 5, 6, 7, 8, 12, or 24 hours. Such frequency is selected to be suitable to the individual patient and its selection is within the ordinary skill of a medical practitioner.

In yet another aspect, a method for providing relief to a discomfort of the eye, comprises: (a) providing a composition comprising glucuronoxylomannan extracted from the mushroom species of *Tremella fuciformis*; and (b) administering to said eye an amount of the composition at a desired frequency sufficient to provide relief to said discomfort of said eye, such as once every 0.5, 1, 2, 3, 4, 5, 6, 7, 8, 12, or 24 hours. Such frequency is selected to be suitable to the individual patient and its selection is within the ordinary skill of a medical practitioner.

In still another aspect, such composition can remain in an ocular environment (such as on an ocular surface) for an extended period of time, such as at least 15 minutes, or at least 30 minutes, or at least 1 hour, or at least 2 hours to 4 hours.

In another aspect, a composition of the present invention is administered topically under an eyelid or on the ocular surface of the subject. In still another aspect, a composition of the present invention is injected into the conjunctival tissue of the subject.

In yet another aspect, a composition of the present invention is administered topically once daily, several times per day (such as 2, 3, 4, 5, 6, 7, 8, 9, 10, 11, or 12 times per day), once every other day, or once a week, as necessary to provide relief to a discomfort of the eye.

In a further aspect, a composition of the present invention can be employed as a vehicle or carrier for a pharmaceutically (in particular, ophthalmically) active ingredient selected from the group consisting of anti-allergic agents, anti-inflammatory agents, anti-infective agents. Such an active ingredient can be present in an amount from about 0.001 to about 2% (by weight) (or from about 0.001 to about 1%, or from about 0.01 to about 0.5%, or from about 0.01 to about 0.2%, or from about 0.01 to about 0.1% by weight). Thus, a composition within the scope of the present invention comprises: (a) a polysaccharide extracted from a plant source; (b) a pharmaceutically acceptable carrier; and a pharmaceutical (in particular, ophthalmic) active ingredient selected from the group consisting of anti-allergic agents, anti-inflammatory agents, anti-infective agents. In one embodiment, a composition within the scope of the present invention comprises: (a) a glucuronoxylomannan or variant thereof extracted from mushroom; (b) a pharmaceutically acceptable carrier; and a pharmaceutical (in particular, ophthalmic) active ingredient selected from the group consisting of anti-allergic agents, anti-inflammatory agents, anti-infective agents. In one embodiment, a composition within the scope of the present invention comprises: (a) a glucuronoxylomannan or variant thereof extracted from *Tremella fuciformis* mushroom; (b) a pharmaceutically acceptable carrier; and a pharmaceutical (in particular, ophthalmic) active ingredient selected from the group consisting of anti-allergic agents, anti-inflammatory agents, anti-infective agents.

Non-limiting examples of anti-allergic agents include antihistamines, mast-cell stabilizers, and combinations thereof.

Non-limiting examples of anti-infectives include antibacterial agents, antifungal agents, antiviral agents, antiprotozoal agents, and combinations thereof.

Non-limiting examples of anti-inflammatory agents include non-steroidal anti-inflammatory drugs ("NSAIDs"), glucocorticoids, antagonists to or inhibitors of proinflammatory cytokines, and combinations thereof.

Examples of these active ingredients may be found in "Goodman & Gilman's The Pharmacological Basis of Therapeutics," L. L. Brunton et al. (Eds), 11$^{th}$ ed., McGraw-Hill Publ., New York, N.Y. (2006).

In one aspect, aqueous compositions of the present invention comprise ingredients and are prepared according methods as follows.

A quantity of purified water of about 50 percent by weight of a desired batch is charged into a sterilized vessel that is equipped with a mixing implement and capability for controlling temperature and sterilized nitrogen purge.

A desired quantity of a polysaccharide extracted from a plant source is sterilely and slowly added to the vessel while the contents are mixed for at least 10 minutes, preferably for at least 30 minutes.

Desired quantities of other optional ingredients, such as pharmaceutically active ingredients, anti-oxidant, surfactant, demulcent, tonicity agent, viscosity-modifying materials are added to the contents of the vessel while mixing. A preservative may or may not be added into the contents of the vessel, as desired.

The contents of the vessel are mixed for at least another 10 minutes, preferably at least 30 minutes.

The remaining amount of purified water is added to the contents of the vessel to yield the final batch quantity. Mixing continues for at least another 10 minutes, preferably at least 30 minutes.

The final mixture is transferred to an autoclave or through a sterilization filter to sterilize before being packaged into final individual units.

Another pharmaceutically acceptable carrier, such as a pharmaceutical buffer may be used in place of the purified water for some other desired embodiments.

The mixture may also include a pharmaceutically acceptable oil, such as a mineral oil or a triglyceride in a desired quantity to produce an emulsion for ophthalmic use.

EXAMPLE C-1

The following ingredients are mixed thoroughly in a sterilized vessel to obtain a composition of the present invention.

TABLE C-1

| Ingredient | Concentration (% by Weight of Final Composition) |
|---|---|
| Glucuronoxylomannan extracted from *Tremella fuciformis* | 0.1-0.5 |
| Purified water | q.s. 100 |
| HCl or NaOH (1N) | For pH adjustment to about 7-7.4 |

EXAMPLE C-2

The following ingredients are mixed thoroughly in a sterilized vessel to obtain a composition of the present invention.

TABLE C-2

| Ingredient | Concentration (% by Weight of Final Composition) |
|---|---|
| Glucuronoxylomannan extracted from *Tremella fuciformis* | 0.1-0.5 |
| Polysorbate 80 | 0.1 |
| Purified water | q.s. 100 |
| HCl or NaOH (1N) | For pH adjustment to about 7-7.4 |

EXAMPLE C-3

The following ingredients are mixed thoroughly in a sterilized vessel to obtain a composition of the present invention.

TABLE C-3

| Ingredient | Concentration (% by Weight of Final Composition) |
|---|---|
| Glucuronoxylomannan extracted from *Tremella fuciformis* | 0.1-0.5 |
| Polysorbate 80 | 0.15 |
| Sodium EDTA | 0.05-0.1 |
| Glycerol | 0.2 |

EXAMPLE C-4

The following ingredients are mixed thoroughly in a sterilized vessel to obtain a composition of the present invention.

TABLE C-4

| Ingredient | Concentration (% by Weight of Final Composition) |
| --- | --- |
| Glucuronoxylomannan extracted from Tremella fuciformis | 0.1-0.5 |
| Polysorbate 80 | 0.15 |
| Sodium EDTA | 0.05-0.1 |
| Glycerol | 0.2 |
| Bromefac | 0.05-0.1 |
| Purified water | q.s. 100 |
| HCl or NaOH (1N) | For pH adjustment to about 7-7.4 |

EXAMPLE C-5

The following ingredients are mixed thoroughly in a sterilized vessel to obtain a composition of the present invention.

TABLE C-5

| Ingredient | Concentration (% by Weight of Final Composition) |
| --- | --- |
| Glucuronoxylomannan extracted from Tremella fuciformis | 0.1-0.5 |
| Polysorbate 80 | 0.15 |
| Sodium EDTA | 0.05-0.1 |
| NaCl | 0.2 |
| Glycerol | For osmolality adjustment to 220-260 mOsm/kg |
| Tobramycin | 0.05-0.1 |
| Purified water | q.s. 100 |
| HCl or NaOH (1N) | For pH adjustment to about 7-7.4 |

EXAMPLE C-6

The following ingredients are mixed thoroughly in a sterilized vessel to obtain a composition of the present invention.

TABLE C-6

| Ingredient | Concentration (% by Weight of Final Composition) |
| --- | --- |
| Glucuronoxylomannan extracted from Tremella fuciformis | 0.1-0.5 |
| Pluronic ® F127 (Polyoxyethylene-polyoxypropylene copolymer | 0.05-0.2 |
| Sodium EDTA | 0.05-0.1 |
| Glycerol | 0.2 |
| Dexamethasone | 0.1 |
| Tobramycin | 0.1 |
| Purified water | q.s. 100 |
| HCl or NaOH (1N) | For pH adjustment to about 7-7.4 |

EXAMPLE C-7

The following ingredients are mixed thoroughly in a sterilized vessel to obtain a composition of the present invention.

TABLE C-7

| Ingredient | Concentration (% by Weight of Final Composition) |
| --- | --- |
| Glucuronoxylomannan extracted from Tremella fuciformis | 0.1-0.5 |
| Carbopol ® 940 | 0.1-0.3 |
| Purified water | q.s. 100 |
| HCl or NaOH (1N) | For pH adjustment to about 7-7.4 |

EXAMPLE C-8

The following ingredients are mixed thoroughly in a sterilized vessel to obtain a composition of the present invention.

TABLE C-8

| Ingredient | Concentration (% by Weight of Final Composition) |
| --- | --- |
| Glucuronoxylomannan extracted from Tremella fuciformis | 0.1-0.5 |
| PEG 400 | 0.05-0.2 |
| Purified water | q.s. 100 |
| HCl or NaOH (1N) | For pH adjustment to about 7-7.4 |

EXAMPLE C-9

The following ingredients are mixed thoroughly in a sterilized vessel to obtain a composition of the present invention.

TABLE C-9

| Ingredient | Concentration (% by Weight of Final Composition) |
| --- | --- |
| Glucuronoxylomannan extracted from Tremella fuciformis | 0.1-0.5 |
| PHMB (polyhexamethylene biguanide, a preservative) | 0.01-0.05 |
| Purified water | q.s. 100 |
| HCl or NaOH (1N) | For pH adjustment to about 7-7.4 |

EXAMPLE C-10

The following ingredients are mixed thoroughly in a sterilized vessel to obtain a composition of the present invention.

TABLE C-10

| Ingredient | Concentration (% by Weight of Final Composition) |
| --- | --- |
| Glucuronoxylomannan extracted from Tremella fuciformis | 0.1-0.5 |
| Pluronic ® F127 (Polyoxyethylene-polyoxypropylene copolymer) | 0.05-0.2 |
| Sodium EDTA | 0.05-0.1 |
| Glycerol | 0.2 |
| Dexamethasone | 0.1 |
| Tobramycin | 0.1 |
| Preservative (such as PHMB) | 0.01-0.05 |
| Purified water | q.s. 100 |
| HCl or NaOH (1N) | For pH adjustment to about 6.7-7.4 |

EXAMPLE C-11

The following ingredients are mixed thoroughly in a sterilized vessel to obtain a composition of the present invention.

TABLE C-11

| Ingredient | Concentration (% by Weight of Final Composition) |
| --- | --- |
| Glucuronoxylomannan extracted from Tremella fuciformis | 0.1-0.5 |
| Polysorbate 80 | 0.1 |
| Sodium EDTA | 0.05 |
| Sodium chloride | 0.5 |
| Borate buffer (pH of 7) | q.s. 100 |

EXAMPLE C-12

The following ingredients are mixed thoroughly in a sterilized vessel to obtain a composition of the present invention.

TABLE C-12

| Ingredient | Concentration (% by Weight of Final Composition) |
| --- | --- |
| Glucuronoxylomannan extracted from Tremella mesenterica | 0.1-0.5 |
| Carboxymethyl cellulose | 0.1 |
| Polysorbate 60 | 0.1 |
| Sodium EDTA | 0.05 |
| Sodium chloride | 0.5 |
| Borate buffer (pH of 7) | q.s. 100 |

EXAMPLE C-13

The following ingredients are mixed thoroughly in a sterilized vessel to obtain a composition of the present invention.

TABLE C-13

| Ingredient | Concentration (% by Weight of Final Composition) |
| --- | --- |
| Glucuronoxylomannan extracted from Tremella fuciformis | 0.1-0.5 |
| Glucuromannoxylomannan extracted from Tremella aurantia | 0.1-0.5 |
| Polysorbate 80 | 0.1 |
| Sodium EDTA | 0.05 |
| Sodium chloride | 0.5 |
| Borate buffer (pH of 7) | q.s. 100 |

EXAMPLE C-14

The following ingredients are mixed thoroughly in a sterilized vessel to obtain a composition of the present invention.

TABLE C-14

| Ingredient | Concentration (% by Weight of Final Composition) |
| --- | --- |
| Glucuronoxylomannan extracted from Tremella fuciformis | 0.1-0.5 |
| Sodium alginate | 0.1-0.3 |
| Polysorbate 60 | 0.1 |
| Sodium EDTA | 0.05 |
| Sodium chloride | 0.5 |
| Borate buffer (pH of 7) | q.s. 100 |

EXAMPLE C-15

The following ingredients are mixed thoroughly in a sterilized vessel to obtain a composition of the present invention.

TABLE C-15

| Ingredient | Concentration (% by Weight of Final Composition) |
| --- | --- |
| Glucuronoxylomannan extracted from Tremella fuciformis | 0.1-0.5 |
| Hydroxypropylmethyl cellulose | 0.1-0.5 |
| Polysorbate 80 | 0.1 |
| Sodium EDTA | 0.05 |
| Sodium chloride | 0.5 |
| Borate buffer (pH of 7) | q.s. 100 |

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. An ophthalmic composition comprising: (a) an ophthalmically acceptable carrier; (b) glucuronoxylomannan extracted from mushroom Tremella fuciformis species, and (c) hydroxypropyl guar or a salt thereof; wherein the ophthalmic composition is a liquid.

2. The ophthalmic composition of claim 1, wherein said glucuronoxylomannan is present at a concentration from about 0.01 to about 5% by weight of the composition.

3. The ophthalmic composition of claim 1, wherein said composition further comprises a surfactant.

4. The ophthalmic composition of claim 1, further comprising polyacrylic acid.

5. The ophthalmic composition of claim 1, wherein the composition is devoid of preservatives that produce discomfort to the eye.

6. The ophthalmic composition of claim 1; further comprising a viscosity-modifying compound.

7. The ophthalmic composition of claim 1; further comprising an active ingredient selected from the group consisting of anti-allergic agents, anti-inflammatory agents, anti-infective agents, and combinations thereof.

8. A method for providing relief to a discomfort of an eye, the method comprising administering to an environment of an affected eye an ophthalmic composition in an amount and at a frequency sufficient to relieve said discomfort; wherein said ophthalmic composition comprises: (a) an ophthalmically acceptable carrier; and (b) glucuronoxylomannan extracted from mushroom Tremella fuciformis species; wherein the ophthalmic composition is a liquid.

9. A method for producing a composition that is capable of providing relief to a discomfort of an eye, the method comprising combining (a) an ophthalmically acceptable carrier; (b) glucuronoxylomannan extracted from Tremella fuciformis species; and (c) hydroxypropyl guar, or a salt thereof; wherein the ophthalmic composition is a liquid.

10. The method of claim 8, wherein said glucuronoxylomannan is present in said composition at a concentration from about 0.01 to about 5% by weight of the composition.

11. The method of claim 8; wherein said ophthalmic composition further comprises polyacrylic acid.

12. The method of claim 8; wherein said ophthalmic composition further comprises alginic acid, hydroxypropyl guar, or a salt thereof.

13. A method for providing relief or amelioration to a disorder of an eye, the method comprising administering to an environment of said eye an ophthalmic composition in an amount and at a frequency sufficient to relieve or ameliorate said disorder; wherein said ophthalmic composition comprises: (a) an ophthalmically acceptable carrier; and (b) glucuronoxylomannan extracted from mushroom *Tremella fuciformis* species; wherein the ophthalmic composition is a liquid.

14. The method of claim 13; wherein said ophthalmic composition further comprises (c) alginic acid, hydroxypropyl guar, or a salt thereof.

15. The ophthalmic composition of claim 1, wherein said glucuronoxylomannan is present at a concentration from about 0.1 to about 0.5% by weight of the composition.

16. The method of claim 8, wherein said glucuronoxylomannan is present in said composition at a concentration from about 0.1 to about 0.5% by weight of the composition.

17. An ophthalmic composition comprising: (a) an ophthalmically acceptable carrier; (b) glucuronoxylomannan extracted from mushroom *Tremella fuciformis* species; (c) alginic acid or a salt thereof; and (d) a surfactant; wherein the ophthalmic composition is a liquid.

18. The ophthalmic composition of claim 17, wherein said glucuronoxylomannan is present at a concentration from about 0.01 to about 5% by weight of the composition.

19. The ophthalmic composition of claim 17, further comprising polyacrylic acid.

20. The ophthalmic composition of claim 17; further comprising a viscosity-modifying compound.

21. The ophthalmic composition of claim 17; further comprising an active ingredient selected from the group consisting of anti-allergic agents, anti-inflammatory agents, anti-infective agents, and combinations thereof.

22. A method for producing a composition that is capable of providing relief to a discomfort of an eye, the method comprising combining (a) an ophthalmically acceptable carrier; (b) glucuronoxylomannan extracted from mushroom *Tremella fuciformis* species; (c) alginic acid or a salt thereof; and (d) a surfactant; wherein the ophthalmic composition is a liquid.

* * * * *